United States Patent

Russell, Jr. et al.

(10) Patent No.: US 7,922,646 B2
(45) Date of Patent: Apr. 12, 2011

(54) PLASTIC BRACHYTHERAPY SOURCES

(75) Inventors: John L. Russell, Jr., Canton, GA (US);
John L. Carden, Jr., Brussells (BE);
Roy Coniglione, Alpharetta, GA (US);
Dominique Moyaux, Brussells (BE)

(73) Assignee: International Brachytherapy, S.A., Seneffe (BE)

( * ) Notice: Subject to any disclaimer, the term of this patent is extended or adjusted under 35 U.S.C. 154(b) by 1395 days.

(21) Appl. No.: 10/568,728

(22) PCT Filed: Aug. 20, 2004

(86) PCT No.: PCT/US2004/027116
§ 371 (c)(1),
(2), (4) Date: Feb. 17, 2006

(87) PCT Pub. No.: WO2005/018736
PCT Pub. Date: Mar. 3, 2005

(65) Prior Publication Data
US 2006/0224035 A1    Oct. 5, 2006

Related U.S. Application Data

(60) Provisional application No. 60/496,474, filed on Aug. 20, 2003.

(51) Int. Cl.
*A61N 5/00* (2006.01)

(52) U.S. Cl. ......................................................... 600/8

(58) Field of Classification Search .................. 600/1–8; 128/898
See application file for complete search history.

(56) References Cited

U.S. PATENT DOCUMENTS

| | | | | | |
|---|---|---|---|---|---|
| 3,351,049 | A | * | 11/1967 | Lawrence | 600/8 |
| 5,342,283 | A | * | 8/1994 | Good | 600/8 |
| 5,498,227 | A | | 3/1996 | Mawad | |
| 6,159,143 | A | * | 12/2000 | Lennox | 600/4 |
| 6,264,599 | B1 | * | 7/2001 | Slater et al. | 600/7 |
| 6,273,851 | B1 | * | 8/2001 | Slater et al. | 600/8 |
| 2002/0022781 | A1 | | 2/2002 | McIntire et al. | |
| 2002/0058057 | A1 | | 5/2002 | Kaplan | |
| 2002/0058853 | A1 | * | 5/2002 | Kaplan | 600/7 |

FOREIGN PATENT DOCUMENTS

EP         0996130 A1 *  4/2000

* cited by examiner

*Primary Examiner* — Samuel G Gilbert
(74) *Attorney, Agent, or Firm* — Gerry J. Elman; Elman Technology Law, P.C.

(57) ABSTRACT

An implantable source (40) of therapeutic radiation for brachytherapy is provided as a sealed, biocompatible capsule (410) of plastic (e.g. polyethylene or PEEK) transparent to the radiation. The capsule contains a radiation source (400) comprising particles of a radioactive isotope (e.g. $Pd^{103}$, $I^{125}$, $Cs^{131}$) in a fluid carrier that is resistant to radiation polymerization but solidifies at elevated temperature. It also has a marker (420), and desirably has a socket (430) which accommodates attaching spacers (660) and makes possible linear strands and planar arrays of the capsules. The spacers may be functional, e.g. heat-generating or medication-releasing.

21 Claims, 5 Drawing Sheets

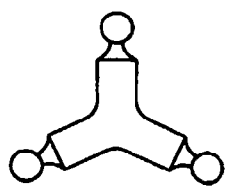
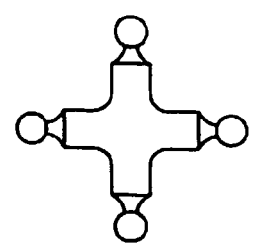
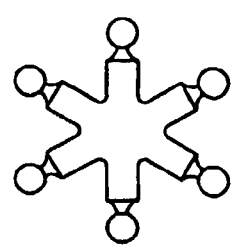
FIG. 7A   FIG. 7B   FIG. 7C   FIG. 7D
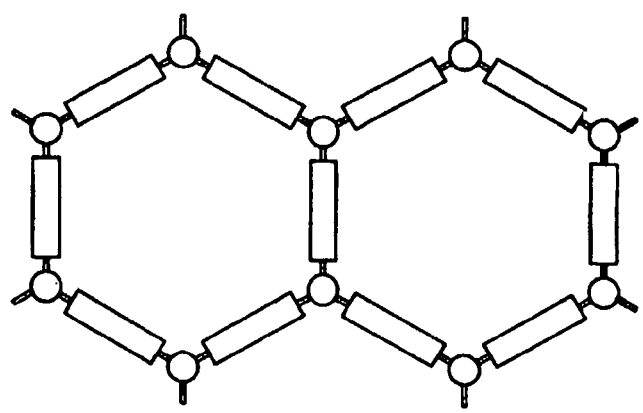
FIG. 8A   FIG. 8B
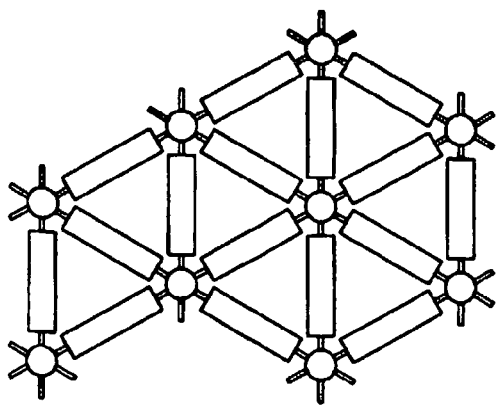
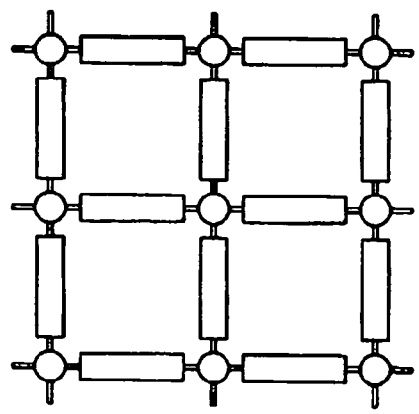
FIG. 8C   FIG. 8D

PLASTIC BRACHYTHERAPY SOURCES

CROSS REFERENCE TO RELATED APPLICATIONS

This application claims priority from U.S. Provisional Patent Application No. 60/496,474, filed Aug. 20, 2003, and is a national phase patent application filing of International Patent Application PCT/US2004/027116, filed Aug. 20, 2004, the contents of both being incorporated by reference herein.

TECHNICAL FIELD

This invention relates to medical devices and their manufacture and use, in particular sources of radiation for treating tumors, namely brachytherapy sources.

BACKGROUND ART

Advancements in the arts of plastic materials and fabrication methods make possible implementation of advanced designs of brachytherapy sources, particularly those sources that emit short-range radiation such as beta particles or low energy x-rays. These types of sources are used for treatment of various types of cancer such as tumors of the prostate, head and neck, lung, liver, breast and others. Typically they are implanted in the tumor, or in the tumor-invaded volume of tissue. There are two types of implants, permanent and temporary. As the categories imply, the temporary implants are associated with equipment for removal of the sources after a few hours or days of radiation treatment. Conversely, permanent implants are placed in the body and remain there for the life of the patient. This is possible because the permanently implanted sources contain a radioisotope with a relatively short half-life, so that the radiation is completely dissipated after a few months, during which time it has destroyed the cancer. And further, the materials of construction of the sources are biocompatible.

The radioisotopes most commonly used in permanent implants today are iodine-125 and palladium-103 encapsulated in very small metallic tubular containers, e.g. of typical approximate dimensions: 4.5 mm in length and 0.8 mm in diameter to form brachytherapy sources. However, the principles and methods taught herein apply as improvements to those and to other sources and source designs, such as custom-molded intracavity irradiators, using any of a variety of radioisotopes such as $Pd^{103}$, $I^{125}$, $Ir^{192}$, $Co^{60}$, $Yb^{196}$, $Sr^{89}$, $Cs^{131}$ and $P^{32}$. Only the short-lived radioisotopes are used in permanent implants.

Such sources used as permanent interstitial implants and with dimensions of approximately 4.5 mm in length and 0.8 mm in diameter are commonly referred to as seeds. Such seeds, are designed around material constraints which include requirements that a) the capsule must be sufficiently transparent to the curative radiation so that it does not unduly diminish or distort the radiation field around the seed, b) yet it must be visible to fluoroscopic or x-ray film examination, so that the physician can determine seed placement, c) it must be strong enough to prevent damage that might permit leakage of the radioactive source material out of the capsule, and d) all surfaces that are in contact with body tissue and fluids must be biocompatible. In addition, it is desirable for the seed to have a shape or other property that permits connecting seeds and spacers so that the implanted seeds are somewhat constrained from migration from the intended implant location.

Currently available seeds meet the above-identified constraints with varying success by balancing conflicting requirements such as strength vs. transparency of the capsule to the emitted curative radiation, or fluoroscopic visibility vs. uniform radiation field. In the following teaching it is shown how the use of a new class of materials to make seeds allows innovative new balances between the several conflicting requirements, with designs that have significant economic and medical advantages over currently available products.

DISCLOSURE OF INVENTION

The new class of materials mentioned earlier belongs to polymers, either organic or inorganic, commonly referred to as plastics. These durable materials are usually composed of light elements that are transparent to low-energy x-rays, many are biocompatible, radioactive material can be dispersed in or contained within them, and they can be precisely and economically formed by current fabrication methods such as milling, injection molding, extrusion, and casting.

One aspect of the present invention is a therapeutic system comprising:
1. a seed comprised of a plastic capsule, containing
2. a source of therapeutic radiation in the plastic capsule,
3. desirably a means of visualizing the seed with diagnostic x-ray, i.e. a marker,
4. optional couplers on each end of the seed to enable connections to auxiliary devices, and
5. optional auxiliary devices including spacers, fixers, imaging enhancers, and dispensers of medication.

As used herein, the term "plastic" refers to inorganic and organic polymers including homopolymers, copolymers and block copolymers, UV and heat curable resins, oligomers, and monomers, and cross-linked polymers.

Another aspect of the invention is a means of fabricating such seeds.

A further aspect of the invention is a means of deploying such seeds.

The titanium metal capsule that is conventionally used to encapsulate radioactive material to make an implantable source (or seed) serves two purposes. It creates a sealed source for purposes of transport and handling, and it also protects the patient from the often-soluble radioactive material in the implanted seed. The major disadvantages of the metal encapsulation are cost, difficulty in fabricating the precise and complex shapes in the encapsulation to serve as couplers and degradation of source performance because of distortion of the radiation field around the seed.

The use of a plastic capsule in accordance with the present invention mitigates all three of these disadvantages. High-strength plastic capsules create a satisfactory sealed source. Fabrication methods are readily available to economically form plastic capsules with the structures required to act as couplers. Most plastics are essentially transparent to the emitted therapeutic radiations and therefore plastic capsules do not significantly distort the radiation field around the seed. And significantly, plastic capsules have an economic advantage because less radioactive material is required to produce a seed, and the manufacturing methods available for producing seeds are fundamentally less expensive than for forming and sealing a metal capsule.

The new concept of using a plastic capsule for a seed has the additional advantage of the possibility of economically forming a special coupler on each end of the seed. The coupler can be used for a variety of functions such as connecting seeds and spacers together to make a linear array or strand of seeds. The coupler also provides a mechanism for attaching a retaining element that can prevent the strand of seeds from leaving the implantation needle until the therapist has positioned the needle satisfactorily. The coupler can also be used to connect the seeds into planar arrays for implantation into surgical wounds to irradiate cancer cells beyond the surgical margin. The coupler can also be used to connect to small dispensers of medicines for treatment of the region in and around the implant. The coupler can also be used to attach elements that cas serce as markers to provide special enhancements for imaging such as enhanced visibility on ultrasound, MRI, fluoroscopy, diagnostic x-ray or during concomitant external beam radiation therapy.

Many of the advantages of a plastic capsule can be realized by simply replacing the metal capsule of conventional seeds. While the wall thickness of the plastic will be greater, and the internal components of the conventional seed design would need to be modified to fit in the smaller available space, the resulting seed performance would be greatly improved.

Additional advantages can be achieved by using a plastic matrix to contain the radioisotope inside the capsule. For example, radioactive iodine contained in an appropriate plastic matrix is released only very slowly in the event of accidental damage to the capsule.

To provide an illustrative summary, the radioisotopes chosen as examples are palladium-103 and iodine-125. Consideration of the differences between these two source materials will illustrate the dependence of plastic seed design on properties such as x-ray energy, isotope concentration, chemical element metabolization by the body, and the nuclear transformation used to produce the isotope. These same principles can then be applied in accordance with the invention to other therapeutically useful isotopes, such as $P^{32}$, $Y^{90}$, $Cs^{131}$, and $Au^{198}$.

Palladium

Palladium-103 may be produced by either of two nuclear transformations: 1) Irradiating palladium-102 in a nuclear reactor, which produces palladium-103 by capture of a neutron i.e., $Pd^{102}$ $(n,\gamma)Pd^{103}$, and 2) Irradiating rhodium-103 with a charged particle from a cyclotron or other accelerator to produce, for example, palladium-103 by the reaction $Rh^{103}$ $(p,n)Pd^{103}$ in which a proton is captured while a neutron is simultaneously ejected from the rhodium nucleus.

The difference between the two products is that in the case of the cyclotron process, the palladium produced can be chemically separated from the rhodium target to yield carrier-free $Pd^{103}$. Carrier-free $Pd^{103}$ has a specific activity of 74,700 Curies per gram. By contrast, the reactor process produces $Pd^{103}$ in a palladium target, thus the $Pd^{103}$ produced cannot be chemically separated from the other Pd isotopes present. This results in $Pd^{103}$ with a much lower specific activity, a result with significant implications for therapeutic seed design.

Of the six stable isotopes in naturally occurring palladium, $Pd^{102}$ amounts to only 1%. In the highest flux nuclear reactors currently operating worldwide, it is only marginally possible to make a useful $Pd^{103}$ seed from neutron capture in a natural palladium target. This limitation can be overcome either by using palladium enriched in the 102 isotope, or by mixing the less expensive reactor-produced $Pd^{103}$ with some carrier-free cyclotron-produced $Pd^{103}$.

Of the several palladium seeds commercially available at this time, all are encapsulated in a titanium metal shell. The amount of source radiation that is emitted from the seed is reduced by 30% to 60% from shielding by the capsule and other internal materials used in the different seed designs. As will be shown in the following, it is possible to design a plastic seed that absorbs less than 2% of the source radiation if the source material is either carrier-free or contains the relatively small amount of carrier normally associated with the radiochemical separation of $Pd^{103}$ from a $Rh^{103}$ accelerator target.

Palladium metal has been reported to be biocompatible. The metal powder has been injected into patients with no reported adverse effects. This means that with the use of plastic materials as revealed in this application, it is possible to consider the design of a permanently implantable seed that dissolves over a time long enough for the radiation to decay away, completing its therapeutic function, and then leaving the treatment volume with no material residue from the therapeutic implant. A biodegradable seed may be desirable for treating certain types of cancer such as breast cancer and some head and neck cancers.

Iodine

The other radioactive isotope widely used for seeds is $I^{125}$. Because of its longer half life, it has a maximum specific activity of 17,600 Curies per gram. To aid in its radiochemical purification, non-radioactive carrier iodine is sometimes added, thus lowering the specific activity.

The ready commercial availability of $I^{125}$ from a number of nuclear reactor facilities around the world makes it less expensive than Pd 103 that is typically produced in cyclotrons. Also, its longer half-life of 57.43 days (vs. 16.99 days for palladium) makes the commercial distribution of seeds produced from it less time-sensitive and thus more reliable. With appropriate adjustments of concentration and isotopic composition, $I^{125}$ can be used in any of the seed geometries described herein for $Pd^{103}$ seeds.

Free iodine in body fluids has a strong tendency to accumulate in the thyroid. In the rare incidence of a damaged seed being implanted in a patient, as much as half of the iodine released by the seed may accumulate in the thyroid gland. Some iodine seeds contain iodine that is chemically or physically constrained in the seed so that in the event of an implanted seed being damaged, the iodine is released slowly over time. This means that much of the iodine will have decayed before it can escape from the seed into the body fluids. One approach to confining the iodine is to chemically confine it within a plastic matrix by fabricating a pellet from the plastic composite and placing the pellet inside the seed capsule.

An alternative way of making an iodine seed is to bond the iodine to a particulate, for example a particle formed from silver-doped activated carbon or zeolite, that slows its release, and then to make a pellet by mixing the powder into a plastic matrix that further slows any release of free iodine. The pellet is further enclosed in a plastic capsule or coating.

BRIEF DESCRIPTION OF THE DRAWINGS

FIGS. 7A to 7D each show a plan view of a connector (having connecting members) which can connect plastic seeds of the present invention into a linear array.

FIGS. 5A to 8D each show diagrammatically a plan view of an array of seeds assembled with connectors similar to those shown in FIGS. 7A to 7D respectively.

MODES FOR CARRYING OUT THE INVENTION

The present invention deals with the fabrication and deployment of a new kind of brachytherapy seed. The seed is comprised of a plastic capsule containing a therapeutic radioactive source, and a marker for the purpose of determining its location within the patient. Optionally incorporation of couplers on each end of the seed enable connections to auxiliary devices including spacers, fixers, imaging enhancers, and dispensers of medication.

Figure 1:
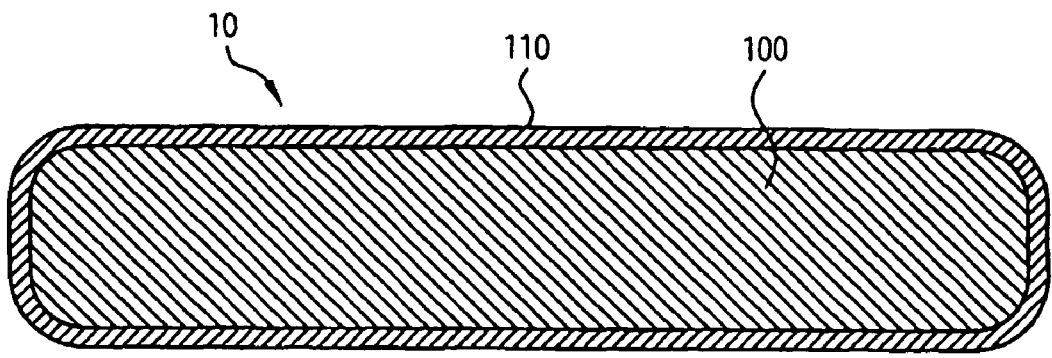
FIG. 1 is a transverse cross-sectional view of a plastic seed of the present invention in which the radioactive source material is substantially uniformly mixed in the solid cylindrical core and is covered with a thin protective layer of non-radioactive plastic.
Figure 2:
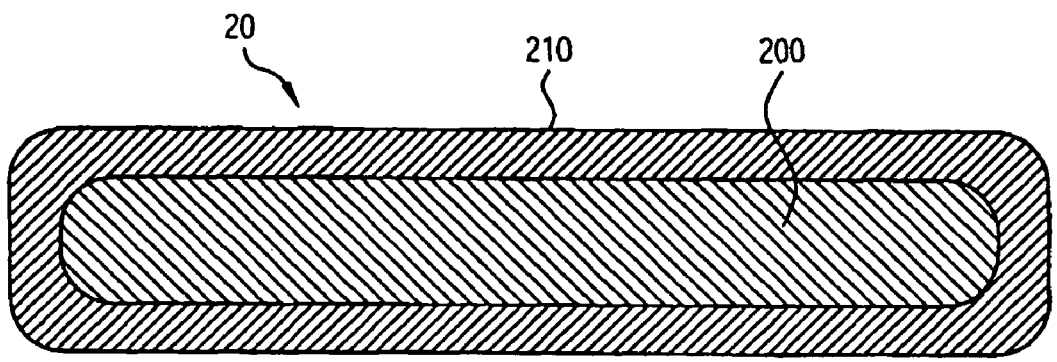
FIG. 2 is a transverse cross-sectional view of a plastic seed in which the radioactive source material is substantially uniformly mixed in the solid cylindrical core and the core is contained in a sealed hollow plastic cylinder, according to the present invention.

FIGS. 1 and 2 are each a transverse cross-sectional view of a plastic seed in which the radioactive source material is substantially uniformly mixed in the solid cylindrical core 100. In FIG. 1, the core 100 is covered with a thin protective layer 110 of non-radioactive plastic. In FIG. 2, the core 200 is contained in a sealed non-radioactive hollow plastic cylinder 210.

Figure 3:
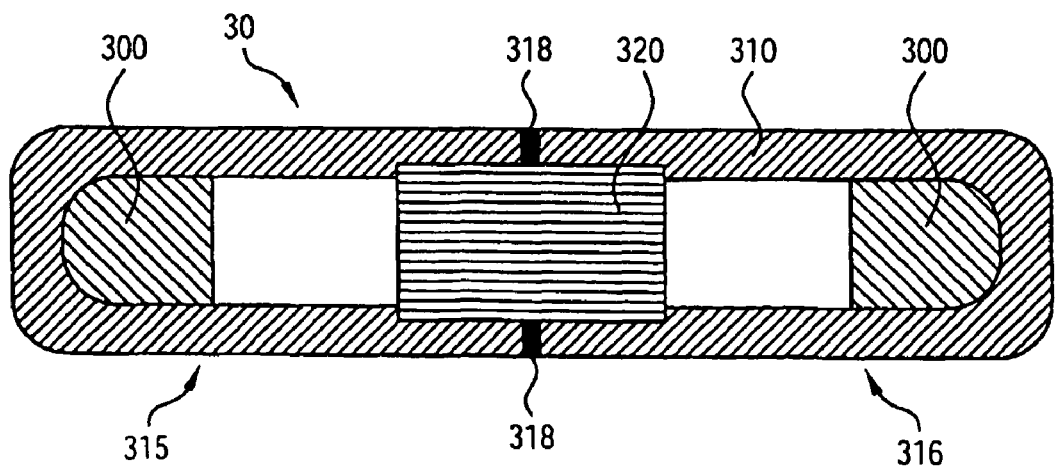
FIG. 3 is a transverse cross-sectional view of a plastic seed of the present invention where the radioactive source material is located in the ends of a cylindrical cavity in a sealed hollow plastic cylinder with a marker located in the center
Figure 4:
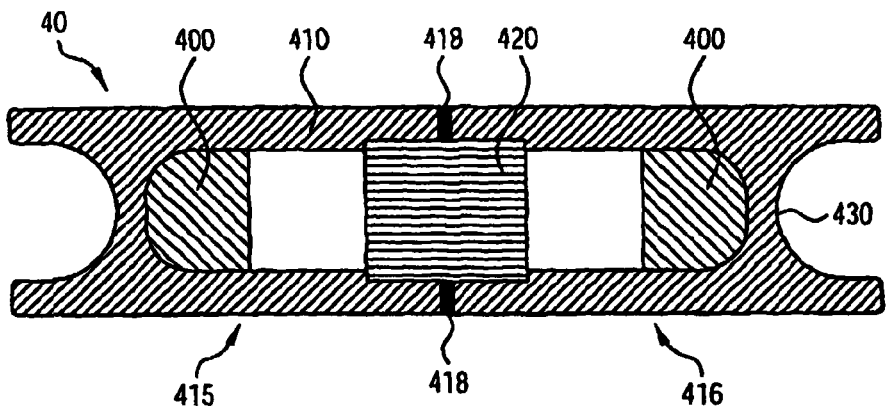
FIG. 4 is a view similar to FIG. 3, but showing an embodiment having a ball joint on each end of the plastic cylinder.

FIGS. 3 and 4 show respectively plastic seeds 30 and 40 in which the radioactive source material 300 and 400 is located at the ends of a cylindrical cavity in a sealed non-radioactive plastic cylinder 310 and 410. The cylindrical cavity also contains a marker 320 and 420, such as a cylinder of metal such as gold, that is readily visible to fluoroscopy or x-ray imaging. The embodiment shown in FIG. 4 differs from that of FIG. 3 in that the sealed hollow non-radioactive plastic cylinder 410 in FIG. 4 has a poppit socket 430 on each end.

The cylinders 310 and 410 are desirably formed from a pair of cup-shaped elements 315, 316 and 415, 416 which respectively are filled with radioactive source material 300 and 400 by a fluid-jet method such as taught in Carden et al., U.S. Pat. No. 6,461,433.

To generate the seed 30 of FIG. 3, for example, one of the cup-shaped elements, e.g. element 316, is then up-ended and topped with a marker 320, which protrudes above the mouth line 318 thereof, e.g. because it rests on a shoulder 319 formed in element 316.

The other cup-shaped element 315 is inverted and then placed atop the aforesaid assembly of elements 316 and 320, and the joint 318 is then sealed, e.g. by ultrasonic welding, laser welding or gluing.

Figure 5:
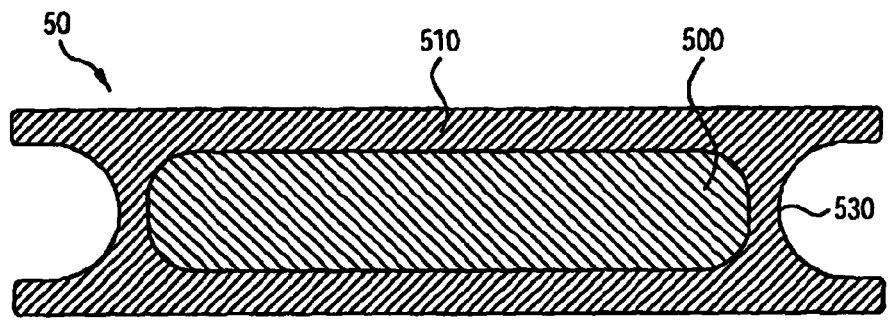
FIG. 5 is a view similar to FIG. 2, but showing an embodiment having a ball joint on each end of the plastic cylinder.
Figure 6:
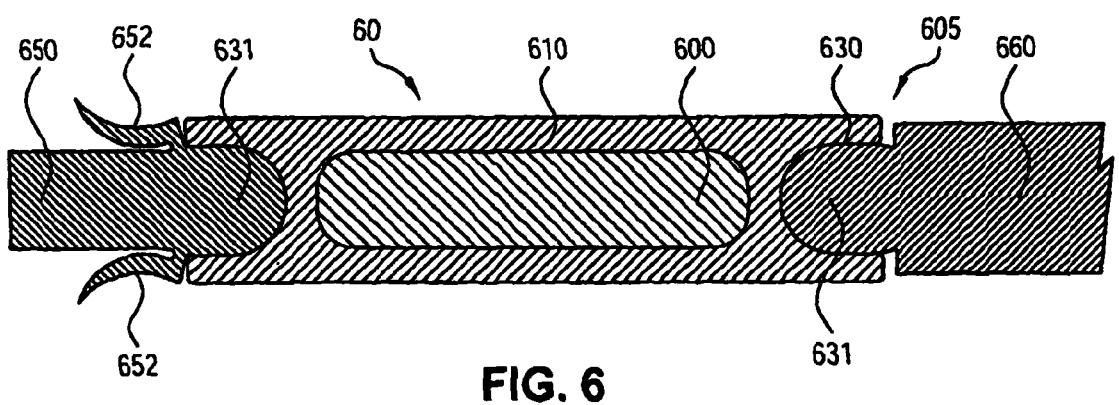
FIG. 6 shows a plastic seed as in FIG. 5 with a fixer attached to one end of the seed and a spacer (a spacing element or other special attachment) attached to the other end of the seed.

FIGS. 5 and 6 each depict a plastic seed 50 and 60 as shown in FIG. 2 with the addition of a ball joint 530 and 630 on each end of the sealed hollow non-radioactive plastic cylinder 510 and 610. FIG. 6 shows an embodiment with further additions: a fixer 650 attached to one end of the seed to prevent longitudinal migration of the seed and spacing element 660 or other special attachment attached to the other end of the seed. The ball 651 of fixer 650 fits like a poppit into a socket 630 of the seed 60. The petals 652 of the fixer 650 spread and stop motion of the seed 60 in either direction.

In some medical procedures, it is desirable to attach several seeds together to make a "string of seeds" or strand. Several means for accomplishing this end have been disclosed in the last few years. For example, these include Langton, et al, U.S. Pat. No. 5,460,592, Coniglione U.S. Pat. Nos. 5,713,828; 6,163,947 and 6,347,443, Horowitz U.S. Pat. No. 4,697,575, Coniglione, et al. U.S. Pat. No. 6,589,502, Grimm U.S. Pat. Nos. 6,010,446 and 6,450,939 and Russell, et al. U.S. Pat. No. 4,784,116. To minimize redundancy in the present disclosure, the disclosure of each patent reference mentioned in this disclosure is incorporated herein to the extent that it is not expressly inconsistent herewith. In the present invention, it is our concept to take advantage of the relative ease with which very small objects can be formed in plastic. That opens the possibility of the kind of seed designs described herein in which the seed ends are specifically shaped to enable exceptional coupling functions.

The present invention provides an innovative modification that is to form a general-purpose rotatable connector on the seed ends. This allows rotation, or bending, of the joint between seed and spacer, thereby avoiding the fragility of prior attempts at joining seeds and spacers. Such a connection 605 is illustrated in FIG. 6. FIGS. 4, 5 and 6, for example, show various embodiments of seeds of the present invention adapted to provide such a connection as ball-and-socket connection 605 by providing a deformable socket 630 into which a poppit ball 631 on a spacer or other functional unit is rotatably and detachably secured.

The joint also can serve the function of an attachment mechanism that permits adding specific functional units to a seed as illustrated in FIG. 6. The functional unit is constructed to provide at least one of the following specific functions:

1. The functional unit is a plug that can optionally be attached to the end of the seed train oriented toward the sharp leading end of the needle. The malleable plug forms a seal (if required) or a simple retaining element, depending on interference with the interior wall of the needle so that the seed train will only leave the needle as a result of the force applied by the therapist during the implant procedure. The plug is desirably made of plastic foam such that it is readily imaged with ultrasound, whereby the physician can easily detect the first seed leaving the needle. Use of such a plug would negate the need for a plug in the sharp end of the needle such is commonly made from bone wax and a cap placed in the needle hub to keep the connected string of seeds from falling out of the needle during handling.

2. The functional unit incorporates a drug delivery system such as a time release coating on a spacer that dispenses, locally, medication such as anti-inflammatory drugs, a local anesthetic, or antibiotics at a controlled rate. Another such functional unit is a spacer or attachment that is composed of a material that couples to a radio frequency electromagnetic field, to allow treatment of an organ with both radiation and hyperthermia.
3. A spacer or attachment that contains a material which improves visibility with medical equipment such as MRI, x-ray, or ultrasound.
4. A half-spacer that separates and positions the seeds by a fixed distance in the needles used for the implant procedures.
5. Other functional units are 2-way, 3-way, 4-way and 6-way connectors as shown in FIGS. 7A to 7D. These connectors can be used to connect seeds in the flexible arrays diagrammed in FIGS. 8A to 8D. The different mesh types produced can be linear, hexagonal, square or triangular, depending upon the requirements of the physician.

Figure 9:
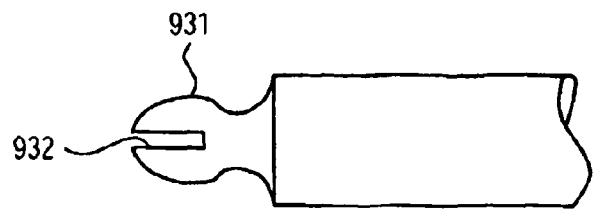
FIG. 9 is a transverse view of a ball joint end of a connector with a slot in the ball to facilitate assembly and disassembly of the joint.

The spherical cavities (sockets) 430, 530 and 630 molded into the ends of the seeds shown in FIGS. 4, 5 and 6 and the spherical ends (balls) 631 of the various functional units are designed and sized so that they snap together for ease of assembly and disassembly and so that they are positively joined. The socket 430, 530 and 630 may have slits formed into its spherical walls so that the ball end of the attachments may flex the socket wall to ease entry of the ball. Alternatively, the construction materials of the ball and/or the socket may be chosen to be pliable enough to allow assembly without need for the slits, and yet be stiff enough to adequately hold the parts together. Or, the ball 631 can be formed with slits 632 to allow it to yield on insertion and snap into place, as shown in FIG. 9. FIG. 9 shows cross-sectional view of the end of a connector ball joint with a slot in the ball to facilitate assembly and disassembly of the joint.

Figure 10:
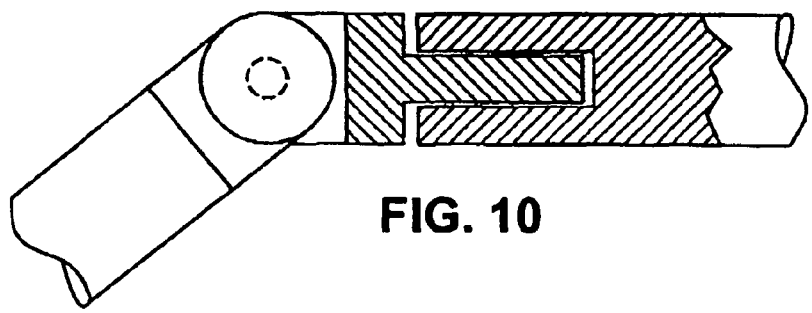
FIG. 10 is a transverse view, in partial cross section, of a flexible joint of the present invention with substantially the same properties of a ball joint. This is a type of rotating shaft coupler that is commonly called a "universal joint" in the field of mechanical engineering.

FIG. 10 illustrates an example of a flexible joint with substantially the properties of a ball joint. This is a type of rotating shaft coupler that is commonly called a "universal joint" in the field of mechanical engineering.

One recurring problem with medical implantation of seeds in tissue is that, occasionally, the seeds jam in the needle and cannot be implanted without removing the needle from the patient. This involves extracting the seeds from the needle, reloading a new needle and attempting to implant a second time. However, the connectors described herein can be manufactured in several diameters. For instance, they can have a diameter larger than that of the seeds, thus preventing the strand from bending or folding inside the needle preventing a jam.

Another recurring problem is that withdrawal of the needle from tissue after depositing seeds or a strand can sometimes alter the position of the implanted devices. This problem is believed to result from the retracting needle acting as a piston creating a reduced hydrostatic pressure against the adjacent end of the seed or strand and the device consequently being pushed toward the needle tip by the higher pressure on its opposite side. This problem can thus be prevented by providing a path for fluid to flow from one side of the seed or spacer to the other. In the present invention, such a flow path can be provided by fluting the seeds and connectors, i.e., by making longitudinal grooves on the surface of the plastic body.

Another type of connector can be fabricated as part of the seed. This differs from the rotatable coupler 60 described in the preceding paragraphs only in that the balls are formed on the ends of the seed and the spherical cavity is in the attachments.

Seeds and spacers may also be formed with a ball on one end and a spherical cavity on the other. This facilitates assembling strands from seeds either with spacers separating the seeds, or alternatively connecting seeds without spacers as requested by some physicians.

Alternatively, the ability to economically fabricate complex shapes in plastic allows those skilled in the art to form a variety of types of connectors that are functionally similar to the preferred ball and spherical cavity joint described. For example FIG. 10 shows a miniature type of mechanical universal joint that behaves much like a ball joint. However, the small size of seeds, places limits on the complexity of practical connector designs for use with them.

Some of the advantages of the rotatable coupler of the present invention are:
1) Seeds and spacers can easily be disassembled and reassembled by the user to meet unanticipated conditions encountered during therapy.
2) The resulting structures firmly snap together making the connection robust while retaining the flexibility associated with the ball-joint design.
3) A variety of auxiliary therapeutic features may be attached to the seeds, using the ball-joint feature.

Figure 11:
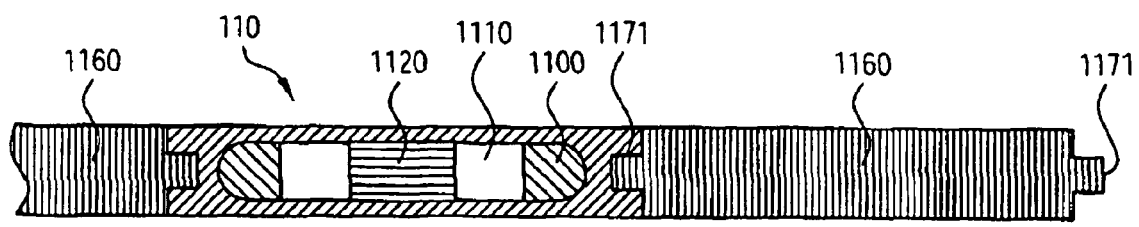
FIG. 11 is a cross sectional view of a plastic seed of the present invention and spacers.

A simple connector that retains most of the advantages of the ball joint is shown in FIG. 11. In this configuration, instead of the spherical cavity 430, 530, 630 of the ball joint, a cylindrical socket 1170 is used on each end of the plastic cylinder. Also shown are spacers 1160 with cylindrical protrusions 1171 on each end, that fit into the cylindrical sockets 1170. The plugs or protrusions 1171 can be held in place by friction, or more robustly, by bonding, using, for example, sonic welding, laser welding or a biocompatible cement.

The seed design illustrated in FIGS. 3, 4 and 5 show the radioactive material in cavities at each end of the seed. The radioactive palladium, iodine or other isotope can be incorporated in a plastic such as an epoxy and then inserted into the seed's plastic capsule. The mixture can first be solidified into a pellet shape and then inserted, or the mixture can be solidified in place in the capsule. However, any method of fixing the radioactive material in place, such as supporting it on or in a graphite, light metal or ceramic pellet, will still retain many of the advantages of an all-plastic seed, and thus are also within the concept of the present invention.

In order to use the potentially more plentiful reactor-produced material in a conventional metal-encapsulated seed, it is necessary to use palladium targets which are highly enriched in the 102 isotope to many times the naturally occurring 1% (see Russell U.S. Pat. No. 4,702,228, claim 1), e.g. by a factor or 20 to 70 corresponding to enrichments of 20% to 70% in $Pd^{102}$. In contrast, it is possible to produce economical plastic seeds from reactor-produced $Pd^{103}$ using targets of palladium enriched to only a few times the naturally occurring 1%, i.e., by a factor of 2 to 6, corresponding to the much more economical enrichments of 2% to 6%.

If the total amount of palladium in the seed is sufficiently high, it will absorb some of the radiation emitted from the $Pd^{103}$. However, it will also be visible on an x-ray film or fluoroscope screen, eliminating the need for a separate x-ray marker in the seed (see FIGS. 1, 2, 5 and 6). As will be shown later, there is a balance between these two effects which depends upon seed design parameters as well as the amount of the diluting non-radioactive palladium present.

EXAMPLES OF PLASTIC SEED DESIGNS

The following are examples of plastic seed designs based on the preceding principles. They illustrate specific embodiments of the invention.

The first configuration to be discussed in detail herein (FIG. 4) illustrates most of the advantages to be gained from encapsulating the radioactive material in a plastic capsule. The seed is a standard dimension, 0.81 mm diameter and 4.5 mm long. In general such seeds may be approximately 0.8 to 1 mm in diameter and approximately 3 to 6 mm long, preferably 4.5 to 5 mm long. The ends of the seed each provide for a general-purpose connector (a ball joint). X-ray visibility is provided by the metal marker cylinder 3 at the seed center. The radioactive isotope 300 and 400 is contained in cavities at symmetrical positions on the seed axis near the ball joints at the ends of the seed.

Cyclotron-produced $Pd^{103}$ has a very high specific activity. If it is diluted by a factor of 20 with non-radioactive palladium to aid in the chemical processing, the specific activity is still 74,700/20 equals 3,735 Curies per gram. Putting 3 mCi of palladium in the seed requires 0.8 micrograms of palladium that results in the palladium blocking only 0.2% of the x-rays from escaping the active region. The plastic capsule is also nearly transparent to the x-rays so that the total transmission of the x-rays in the direction perpendicular to the seed axis is about 97%. This is to be compared with about 50% transmission for most seeds currently on the market.

The high specific activity of $I^{125}$ means that it also can be used in the configuration shown in FIG. 4 and will have equally low absorption losses.

Palladium and iodine both emit low-energy electrons and soft x-rays that do not have therapeutic value because of their short range. In fact, such radiations, if not blocked to prevent them from interacting with the tissue very close to the surface of the seed, have the potential for causing excessive local radiation damage. The titanium shell of traditional devices effectively blocks these radiations, but at the same time blocks a substantial percentage (40% to 60%) of the therapeutic radiation created in the seed by the radioisotope. The plastic wall of the current invention acts as a much more efficient filter, removing the potentially harmful low energy emissions while allowing essentially all (>97%) of the therapeutic radiation to escape from the capsule. For a typical organic plastic material forming the wall of a device such as that shown in FIG. 4, a wall thickness of between 150 and 350 micrometers provides this balanced filtering effect. The plastic wall of the capsule capsule illustrated in FIG. 4 is preferably approximately 0.2 mm thick.

The efficient filtering effect of the plastic wall of the current invention also provides a very important improvement in the safety of seeds implanted in patients. On rare occasions, seeds are damaged before or during implantation and such a damaged seed can release some or all of the radioisotope it contains into the body of the patient. Because the wall of the plastic seed of the current invention provides very efficient filtering, much less isotope must be incorporated into the seed to produce a given therapeutic effect relative to a conventional seed with a titanium shell. For example, an $I^{125}$ seed with a wall that was perfectly transparent to the therapeutic radiation produced by the isotope would require a certain amount of radioisotope to deliver a specified therapeutic radiation dose. By comparison, titanium encapsulated seeds currently on the market require from 70% to 120% more $I^{125}$ to produce the same therapeutic dose depending on the specific seed design. Current palladium seeds typically require 100% more radioisotope. Plastic seeds of either isotope of the current invention would require less than 10% excess isotope representing a significant improvement in safety for the patient.

The specific activity of reactor-produced $Pd^{103}$ depends upon several factors. These include the intensity of the neutron flux in the reactor, the reactor operating cycle and schedule, and the $Pd^{102}$ enrichment of the palladium target. A flux of $2 \times 10^{15}$ neutrons per $cm^2$ per second and an operating cycle of about 23 days on and 4 days down are characteristic of the HFIR test reactor at Oak Ridge National Laboratory. Two cycles of irradiation of a palladium target enriched to a few times the 1% natural abundance to 6% $Pd^{103}$ will produce palladium with a specific activity of approximately 10 Curies/gram after allowing 17 days for the high-energy gamma emitter, metastable $Pd^{109}$, to decay to insignificance. If the length of the two sources 400 in FIG. 4 is extended to 1 mm, nearly filling the cavity not occupied by the marker 420, the total source volume is 0.00025 $cm^3$. Three mCi of $Pd^{103}$ with specific activity of 10 Curies/gram has a mass of 0.0003 grams. The density of palladium in the source region is then 0.0003/0.00025, which equals 1.2 grams. The transmission of palladium x-ray radiation out of the source capsule perpendicular to the seed axis is 0.74. The seed therefore has an apparent activity of 0.74×3 equals 2.2 mCi. These considerations indicate that it is possible to manufacture a commercial palladium seed of this design using palladium enriched to 6% in $Pd^{103}$.

Those skilled in the art, using the computational methods illustrated in the previous paragraph can show that increasing the source volume permits using lower specific-activity palladium. The source volume can be increased in the plastic seed design by increasing the length of the source region as is illustrated in FIGS. 5 and 2. A further increase in source volume can be attained by increasing the source radius as shown in FIG. 1. It is possible to produce a useful palladium seed using the inventive embodiment shown in FIG. 1 with reactor-produced palladium enriched to only 2% in $Pd^{103}$.

Seed designs, in which there is significant loss of the source radiation from self-absorption in the source material, also have sufficient absorption of x-rays to be visible on a fluoroscope screen or diagnostic x-ray plate. For transmissions of about 0.5 or more, the seeds are sufficiently visible for the post-implant documentation. For some designs this negates the need for a conventional heavy-metal x-ray marker in the seed.

Plastic Construction Materials

Plastic materials to be considered in design of plastic capsules and spacers in accordance with the present invention include such biocompatible plastics as PEEK-OPTIMA® manufactured by Invibio, VECTRA liquid crystal polymer manufactured by Ticona LLC, ultra-high-density polyethylene and polypropylene. The high melting temperature of poly ether ether ketone (PEEK, 343 degrees Celsius) makes this a preferred choice, especially if high temperatures are expected to be encountered, e.g. in sterilization. However, there are many other plastic materials which those skilled in materials science will find to be appropriate and satisfactory for a variety of different applications.

Composition of Radioactive Source Material for a $Pd^{103}$ Seed of the Current Invention The following example is intended to illustrate the formulation of a source material that is essentially free of internal x-ray absorption and is thus produced from carrier free $Pd^{103}$ from a proton accelerator. Many persons skilled in the art are familiar with methods for extracting $Pd^{103}$ from rhodium cyclotron targets and its subsequent purification. An example includes Carden, U.S. Pat. No. 5,405,309. At the end of the purification process, the solution containing the $Pd^{103}$ is concentrated into a very small mass of material, for instance 25 Ci of $Pd^{103}$ contained in a final mass of approximately 200 mg. This concentration step is necessary for two reasons: 1) because the volume available within the seed for the source material to occupy is very small (approximately 0.8 µL), the $Pd^{103}$ activity per unit of source material must be correspondingly large (approximately 20 Ci per ml) and 2) the radioactive concentrate acts as a diluent in the solidified polymer, and if this effect is too large, the curing properties and mechanical strength of the cured polymer may be adversely modified.

A desirable property of the source material is that it solidifies into a hard and durable "pellet" once it has been delivered to the desired location within the seed. To satisfy this requirement, we have developed an epoxy formulation with thermally initiated polymerization.

Finally, delivery of the source material into the desired location within the seed is problematic. When considered in relative terms, the problem can be summarized as the necessity to deliver a very precise volume of fluid to the bottom of a long narrow cavity. A solution to this problem is to use a single-jet, drop-on-demand, fluid-jet print head to deliver a precise number of drops into the cavity of the seed shell. This however adds the requirement that the source material must have a viscosity and surface tension that will facilitate jetting. Given below are two examples of formulations found to satisfy the aforesaid requirements (percentages being weight percent):

Formulation 1
1. Radioactive residue (17 wt. %)
2. Triethylene glycol divinyl ether (55 wt. %)
3. Cycloaliphatic epoxide resin (CYRACURE UVR-6110 resin from Union Carbide) (18 wt. %)
4. Boron trifluoride monoethyl amine (2 wt. %)
5. Propylene carbonate (8 wt. %)

To perform the manufacturing method disclosed herein, the radioactive residue is dissolved in components 2 and 3, while component 4 is dissolved in a portion of the solvent 5. All of the liquids are then combined to form the source material. The source material is then jetted in the proper quantity into the volume of the seed shell that it is to occupy, and the source material is then heated to approximately 190° C., to initiate curing.

Formulation 2
1. Pd-103 residue (13 wt. %)
2. Cyclohexanone (70 wt. %)
3. Liquid epoxy resin (ARALDITE 6005, bisphenol A diglycidyl ether polymer) (15 wt. %)
4. Boron trifluoride-ethylamine complex (2 wt. %)

To perform the manufacturing method disclosed herein, components 2 and 3 are combined, and then component 4 is added. Component 1 is then combined to form the source material. The source material is then jetted in the proper quantity into the volume of the seed shell that it is to occupy, and the source material is then heated to approximately 130° C., to cure for approximately 1.5 hr.

Those skilled in the art will know that the physical and chemical properties of the above-described formulations can be modified by the addition or substitution of other chemical ingredients to get desired results.

Figure 12:
FIG. 12 is a transverse view of a spacer with a poppit ball at each end.
Figure 13:
FIG. 13 is a transverse view of a functional unit in accordance with the present invention.

As shown in FIGS. 7A and 12 a spacer typically has a poppit ball on each end, making it a two-way spacer. Alternatively, as shown in FIG. 13, a functional unit may have a single poppit ball intended to mate with a socket on a seed of the present invention, having a one-way function.

As shown in FIG. 7B, a spacer may be provided in a three-way orientation, and in FIG. 7C, a spacer with a four-way orientation is shown. FIG. 7D shows a spacer with a six-way orientation.

FIG. 8A shows three seeds in linear array, as joined by two respective two-way spacers and as terminated with a one-way spacer (functional unit) at each end.

FIG. 8B shows a hexagonal array formed by joining a multiplicity of seeds of the present invention with three-way spacers.

FIG. 8C shows a square array formed by joining a multiplicity of seeds of the present invention with four-way spacers.

FIG. 8D shows a triangular array formed by joining a multiplicity of seeds of the present invention with six-way spacers. Those skilled in the art will appreciate that these configurations are illustrative rather than exhaustive of the variations which may be applied.

The functional unit is a plug that can optionally be attached to the end of the seed train oriented toward the sharp leading end of the needle. The malleable plug forms a seal (if required) or a simple retaining element, depending on interference with the interior wall of the needle so that the seed train will only leave the needle as a result of the force applied by the therapist during the implant procedure. The plug is desirably made of plastic foam such that it is readily imaged with ultrasound, whereby the physician can easily detect the first seed leaving the needle. Use of such a plug would negate the need for a plug in the sharp end of the needle such is commonly made from bone wax and a cap placed in the needle hub to keep the connected string of seeds from falling out of the needle during handling.

The functional unit incorporates a drug delivery system such as a time release coating on a spacer (not separately illustrated) [GJE1]that dispenses, locally, medication such as anti-inflammatory drugs, a local anesthetic, or antibiotics at a controlled rate. Another such functional unit shown in FIG. 12 is a spacer or attachment that is composed of a material that couples to a radio frequency electromagnetic field, to allow treatment of an organ with both radiation and hyperthermia.

A spacer or attachment that contains a material which improves visibility with medical equipment such as MRI, x-ray, or ultrasound.

A half-spacer, illustrated in FIG. 13, that separates and positions the seeds by a fixed distance in the needles used for the implant procedures.

Other functional units are 2-way, 3-way, 4-way and 6-way connecters as shown in FIGS. 7A to 7D. These connecters can be used to connect seeds in the flexible arrays diagrammed in FIGS. 8A to 8D. The different mesh types produced can be linear, hexagonal, square or triangular, depending upon the requirements of the physician.

The spherical cavities poppit sockets) 430, 530 and 630 molded into the ends of the seeds shown in FIGS. 4, 5 and 6 and the spherical ends (balls) 631 of the various functional units are designed and sized so that they snap together for ease of assembly and disassembly and so that they are positively joined.

Figure 14:
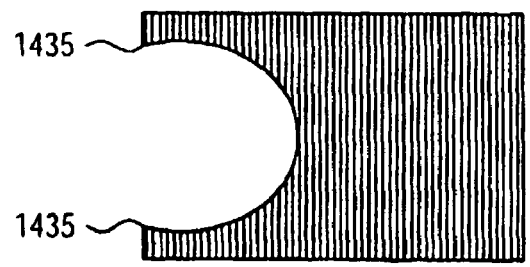
FIG. 14 is a diagrammatic cross-section of a poppit socket incorporated in the end of a plastic seed of the invention.
Figure 15:
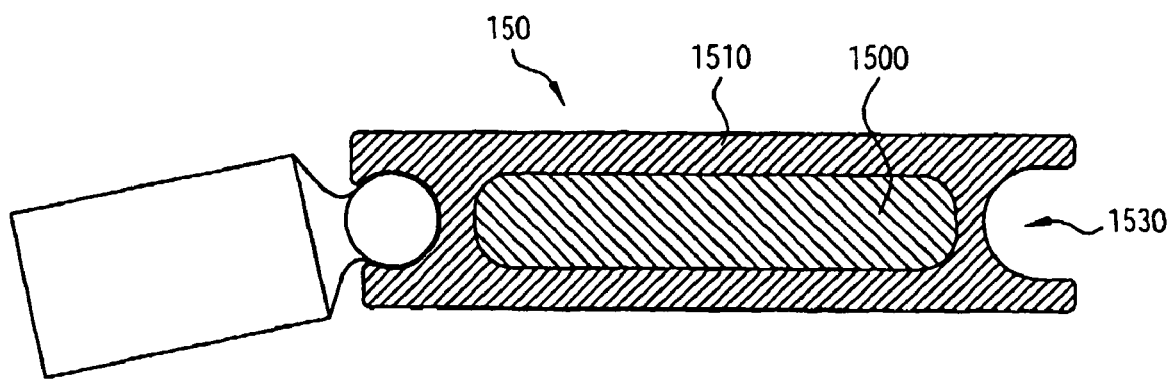
FIG. 15 is a transverse view in partial cross section of a seed of the present invention attached to a functional unit.

The socket 430, 530 and 630 is illustrated in FIG. 14 as a blown up cross section. To be noted is the protrusion 1435 at the entry to provide better fit between ball and socket joint and hence removing the possibility of slipping between the seed and functional unit. The socket 430, 530 and 630 may have slits formed into its spherical walls so that the ball end of the attachments may flex the socket wall to ease entry of the ball. Alternatively, the construction materials of the ball and/or the socket may be chosen to be pliable enough to allow assembly without need for the slits, and yet be stiff enough to adequately hold the parts together. Or, the ball 931 can be formed with slits 932 to allow it to yield on insertion and snap into place, as shown in FIG. 9. FIG. 9 shows side view of the end of a connector ball joint with a slot in the ball to facilitate assembly and disassembly of the joint.

INDUSTRIAL APPLICABILITY

The present invention provides a brachytherapy device comprising a plastic seed containing radioactive source material with the added benefit of attaching specific functional units such as markers, plugs, fixers, medication dispensers, seed-containing material to allow hyperthermia. These are some examples of functional unit, but the list is not complete. The present invention offers further advantages such as uniform radiation field, up to about 97% transparency of the seed to the emitted curative radiation, fluoroscopic visibility, precise and economical manufacturing of seed by fabrication methods such as milling, injection molding, extrusion and casting.

What is claimed is:

1. An implantable brachytherapy source for use in radiation treatment of an affected tissue region, said implantable brachytherapy source comprising a functional unit having one or more ball joints, and a biocompatible capsule having two ends, said biocompatible capsule having a socket at each end adapted to be affixed to a ball joint of said functional unit to form a linear strand or a planar array, wherein said biocompatible capsule is made of mechanically strong, biocompatible, plastic material that is transparent to therapeutic radiation, and wherein said biocompatible capsule contains therein a radioactive seed comprising:
 (a) an epoxy based fluid carrier that is resistant to radiation polymerization in its fluid phase, but can be induced to solidify by raising its temperature;
 (b) a marker visible by x-ray, ultrasound, or nuclear magnetic resonance imaging; and
 (c) a source of therapeutic radiation comprising a radioactive isotope selected from the group consisting of Pd-103, I-125, and Cs-131;
wherein said radioactive isotope is substantially uniformly mixed in said fluid carrier.

2. The implantable brachytherapy source of claim 1, wherein said plastic material is high density polyethylene or polyetheretherketone (PEEK).

3. The implantable brachytherapy source of claim 1, wherein said plastic material is medical grade polyetheretherketone (PEEK).

4. The implantable brachytherapy source of claim 1, wherein said functional unit has 1, 2 ,3, 4, or 6 ball joints adapted to be affixed to a socket of said biocompatible capsules to form a linear strand or a planar array having triangular, square, and hexagonal patterns comprising said biocompatible capsule and said functional unit.

5. The implantable brachytherapy source of claim 1, wherein said functional unit further comprises a drug delivery system or coating on said functional unit that controllably releases an anti-inflammatory drug, a local anesthetic, an antibiotic, an anti-cancer adjuvant, a radiation enhancing drug, or other medication.

6. The implantable brachytherapy source of claim 1, wherein said functional unit further comprises a material that absorbs radio waves to produce heat for treating an organ with hyperthermia.

7. The implantable brachytherapy source of claim 1, wherein said functional unit further comprises an expandable petal or barb, whereby motion through the site of implantation is hindered.

8. The implantable brachytherapy source of claim 1, further comprising a functional unit having one ball joint, wherein said functional unit having one ball joint comprises a malleable plug comprising a plastic foam which is readily imaged with ultrasound.

9. The implantable brachytherapy source of claim 1, wherein said fluid carrier comprises an epoxy based fluid that is substantially uniformly mixed with the radioisotope to form a carrier fluid that can be jetted through an ink-jet head into said biocompatible capsule, where curing is initiated by heating.

10. The implantable brachytherapy source of claim 1, wherein said fluid carrier comprises, by weight percent, about
 (1) Radioactive residue 17%,
 (2) Triethyleneglycoldivinylether 55%,
 (3) Cycloaliphatic epoxide resin 18%,
 (4) Borontrifluoride monoethylamine 2%, and
 (5) Propylene carbonate 8%.

11. The implantable brachytherapy source of claim 1, wherein said marker is replaced by a nonradioactive isotope of said radioactive isotope such that the resulting radioactive seed is visible by magnetic resonance imaging (MRI), fluoroscopy, or x-ray film imaging.

12. A brachytherapy device for use in radiation treatment of an affected tissue region, the brachytherapy device comprising a functional unit having one or more ball joint elements, and a sealed hollow outside cylindrical capsule having two ends, said capsule comprising a biocompatible nonabsorbable polymeric matrix and having a socket at each end adapted to be affixed to a ball joint element of said functional unit to form a linear strand or a planar array and wherein said hollow outside cylindrical capsule surrounds an inside cylindrical solid radioactive seed comprising a marker and a source of therapeutic radiation uniformly mixed with and dispersed throughout an epoxy based fluid carrier.

13. The brachytherapy device of claim 12, wherein the radioactive isotope is comprised of a powder selected from the group consisting of Pd-103, I-125 and Cs-131.

14. The brachytherapy device of claim 12, wherein the biocompatible nonabsorbable polymeric matrix is selected from the group consisting of high density polyethylene, high density polyaryletheretherketone and medical grade polyaryletheretherketone.

15. The brachytherapy device of claim 12, further comprising a radiographically detectable element for locating the brachytherapy device within the body of a patient.

16. The brachytherapy device of claim 12, wherein said functional unit having one or more ball joint elements is biodegradable.

17. The brachytherapy device of claim 16, wherein said biodegradable functional unit is comprised of one ball joint element, two ball joint elements, three ball joint elements, four ball joint elements or six ball joint elements.

18. A method of making a solid plastic radioactive seed comprising the steps of:
 (a) mixing a source of therapeutic radiation dispersed in an epoxy based fluid carrier, with a marker and a biocompatible nonabsorbable polymeric matrix to form a fluid homogenous radioactive mixture;
 (b) injecting said fluid homogenous radioactive mixture through an ink-jet head into a biocompatible capsule; and
 (c) heating said biocompatible capsule to cure the fluid homogenous radioactive mixture to form said solid plastic radioactive seed;
wherein said source of therapeutic radiation comprises a radioactive isotope selected from the group consisting of Pd-103, I-125, and Cs-131, wherein said biocompatible capsule is made of mechanically strong, biocompatible, plastic material that is transparent to therapeutic radiation, and wherein said biocompatible capsule has a socket at each end adapted to be affixed to one or more ball joints of a functional unit adapted to being assembled to form a linear strand or a planar array comprising a multiplicity of said biocompatible capsule and said functional unit.

19. The method according to claim 18, wherein said marker comprises a radiographically detectible element which is mixed with said radioactive isotope and biocompatible nonabsorbable polymeric matrix of step (a), whereby said radiographically detectible element aids in locating the brachytherapy device within the body of a patient.

20. The method according to claim 18, wherein the radioactive isotope is comprised of a powder selected from the group consisting of Pd-103, I-125 and Cs-131.

21. The procccs method according to claim 18 wherein the biocompatible nonabsorbable polymeric matrix is selected from the group consisting of high density polyethylene, high density polyaryletheretherketone and medical grade polyaryletheretherketone.

* * * * *